United States Patent [19]

Marrocco, III et al.

[11] Patent Number: 5,648,448

[45] Date of Patent: Jul. 15, 1997

[54] METHOD OF PREPARATION OF POLYQUINOLINES

[75] Inventors: Matthew L. Marrocco, III, Santa Ana; Ying Wang, Diamond Bar, both of Calif.

[73] Assignee: Hitachi Chemical Company, Ltd., Tokyo, Japan

[21] Appl. No.: 469,993

[22] Filed: Jun. 6, 1995

[51] Int. Cl.$^6$ .............................. C08G 8/02; C08G 14/00
[52] U.S. Cl. .................... 528/125; 528/126; 528/210; 528/211; 528/219; 528/401; 528/423; 428/364; 428/221; 428/901; 361/326
[58] Field of Search ........................ 528/125, 126, 528/210, 211, 219, 401, 423; 428/364, 221, 901; 361/326

[56] References Cited

U.S. PATENT DOCUMENTS

| | | | |
|---|---|---|---|
| 4,000,187 | 12/1976 | Stille | 528/125 |
| 4,519,937 | 5/1985 | Papir | 252/500 |
| 4,727,135 | 2/1988 | Chiang et al. | 528/423 |
| 4,966,954 | 10/1990 | Moore et al. | 528/125 |
| 5,017,677 | 5/1991 | Stille | 528/125 |
| 5,053,478 | 10/1991 | Moore et al. | 528/125 |
| 5,149,773 | 9/1992 | Chiang et al. | 528/423 |
| 5,247,050 | 9/1993 | Hendricks | 528/125 |

OTHER PUBLICATIONS

Singh et al., "Synthesis and Physical Properties of Amorphous Poly(aryl ether isoquinolines)s," *Macromolecules*, 1992, 25, pp. 1033–1040.

*Primary Examiner*—Samuel A. Acquah
*Attorney, Agent, or Firm*—Antonelli, Terry, Stout & Kraus, LLP

[57] ABSTRACT

New polyquinoline polymers are provided, as well as new methods for preparing the polyquinoline polymers using a novel combination of monomers. The polyquinoline polymers comprise repeat units comprising at least one quinoline nucleus and at least one ether linkage and having as end groups either fluoro groups or hydroxy groups or a combination of fluoro and hydroxy groups. The polymers are formed by providing a monomer comprising two fluoro groups, where each such fluoro group is activated by a quinoline nucleus, a diol monomer provided in the form of its bis-oxide salt, or in the presence of a base capable of deprotonating the diol and reacting the difluoro and diol monomers together in a dipolar solvent to form the polyquinoline polymer. In an alternative embodiment, the polyquinoline polymers of the present invention are formed by reacting a fluoro hydroxy monomer comprising a quinoline nucleus containing one activated fluoro group and one hydroxy group in the presence of a base and a dipolar solvent to form said polymer. In yet another alternative embodiment, the polyquinoline polymer is formed by providing a monomer which comprises a quinoline nucleus containing one activated fluoro group and one hydroxy group and treating the monomer with a base to form an oxide salt and reacting the monomer salt in a dipolar solvent to form said polymer.

20 Claims, 3 Drawing Sheets

METHOD OF PREPARATION OF POLYQUINOLINES

FIELD OF THE INVENTION

This invention relates to new methods for preparing polyquinoline polymers, to the novel monomers used to prepare the polymers, and to the polymers themselves.

BACKGROUND OF THE INVENTION

Polyquinoline polymers are useful in a broad range of electronics and microelectronics applications, including planarizing dielectric layers in integrated circuit manufacture, passivation layers, as protective coatings and potting compounds, as adhesives, as resins for printed wiring board fabrication, as dielectric materials, as coating applications for liquid crystal displays, flat panel television, solar windows, and the like, as fibers, and as high-strength stable films.

Methods of preparing polyquinolines by the Friedlander condensation reaction are disclosed in U.S. Pat. No. 4,000,187 which issued to J. Stills on Dec. 28, 1976. By means of the Friedlander reaction, polyquinoline polymers are prepared from the reaction of what is called a type AA compound, i.e., an aromatic amino carbonyl which contains two sets of ortho-amino carbonyl functions attached to an aromatic nucleus, with what is called a type BB compound, i.e., a bis-methylene ketone compound. Polyquinoline polymers may also be prepared from type AB compounds, i.e., compounds which incorporate both an ortho-amino carbonyl function and a methylene ketone function on an aromatic nucleus.

In conducting the Friedlander reaction, the AA and BB or AB type compounds are typically reacted in the presence of a phosphate catalyst in m-cresol solvent. Such phosphate/cresol catalyst systems are expensive and cresol is difficult to work with.

It is desired to provide a process for forming polyquinolines which is economical and which does not require cresol as a solvent.

SUMMARY OF THE INVENTION

The present invention provides new and economical methods for forming polyquinoline polymers, the novel monomers used to form the polymers, and the polymers themselves.

In a preferred embodiment, the method for forming polyquinoline polymers of the present invention comprises the steps of providing a monomer comprising two fluoro groups, wherein each such fluoro group is activated by a quinoline nucleus. A diol monomer is provided in the form of its bis-oxide salt or is in the presence of a base capable of deprotonating the diol. The difluoro monomer is reacted with the diol monomer in a dipolar solvent to thereby form the polyquinoline polymer.

In another embodiment, the method for forming the polyquinoline polymers of the present invention comprises reacting a fluoro hydroxy monomer comprising a quinoline nucleus containing one activated fluoro group and one hydroxy group in the presence of a base in a dipolar solvent to thereby form the polyquinoline polymer.

In yet another embodiment, the method for forming the polyquinoline polymers of the present invention comprises providing a monomer which comprises a quinoline nucleus containing one activated fluoro group and one hydroxy group. The monomer is treated with a base to form an oxide salt, and the monomer salt is reacted in a dipolar solvent to thereby form the polyquinoline polymer.

In another aspect of the present invention, a polyquinoline polymer is provided which comprises repeat units comprising at least one quinoline nucleus and at least one ether linkage, and having as end groups either fluoro groups or hydroxy groups, or a combination of fluoro and hydroxy groups.

In another aspect of the present invention, monomers useful for forming polyquinoline polymers of the present invention are provided.

In yet another aspect of the present invention, multi-chip modules, capacitors, integrated circuits, films, and fibers formed from the polymers provided in accordance with practice of the present invention are provided.

BRIEF DESCRIPTION OF THE DRAWINGS

These and other features, aspects and advantages of the present invention will be more fully understood when considered with respect to the following detailed description, appended claims, and accompanying drawings, wherein:

DETAILED DESCRIPTION

Figure 1:
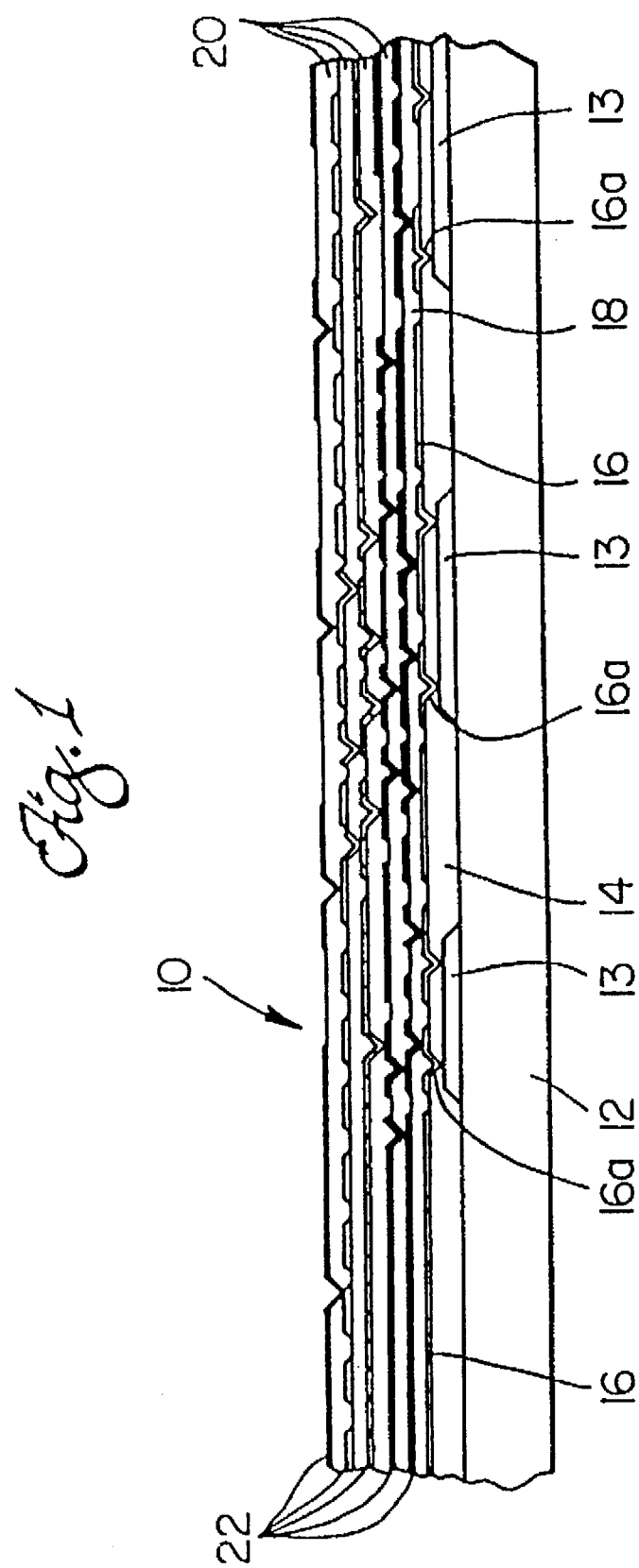
FIG. 1 is a semi-schematic fragmentary cross sectional side view of a multi-chip module provided in accordance with practice of the present invention.

This invention is directed to a new class of polyquinoline polymers, to the monomers which are used for their preparation, and to various products formed from the polymers.

The polymers provided in accordance with practice of the present invention can be formed from a single monomer containing one each of two functional group types, typically called an AB monomer, or from two monomers, each containing two of the same functional groups, typically called type AA and type BB monomers. The terms "type AA monomer," "type BB monomer," and "type AB monomer" are commonly used for describing monomers used in condensation polymerization systems. For example, one such system is described in U.S. Pat. No. 4,000,187, which is directed to the use of Friedlander reactions to prepare polyquinolines by reacting an aromatic amino carbonyl compound containing two sets of ortho-amino aldehyde or ortho-amino ketone functions (in this case, the AA monomer) with a monomer containing two ketone functions having a methylene group adjacent each function (in this case, the BB monomer). U.S. Pat. No. 4,000,187 is incorporated herein by this reference.

The polyquinoline homopolymers of the present invention are prepared either from two monomers, i.e., from a type AA monomer and a type BB monomer, or from a single type AB monomer. Polyquinoline copolymers are prepared from mixtures of two or more type AA monomers with one or more type BB monomers; or one or more type AB monomers with one or more type AA, or one or more type BB monomers; or two or more different AB monomers.

The type AA monomer of the present invention comprises two fluoro groups, where each such fluoro group is activated by a quinoline nucleus. The type BB monomer of the present invention is a diol which may be any diol stable to the basic conditions of the reaction. The difluoro (type AA) monomer is reacted with the diol (type BB) monomer in the presence of a base in a dipolar solvent to thereby form the polyquinoline polymer. The type AB monomers of the present invention are fluorohydroxy monomers which comprise a quinoline nucleus containing a single activated fluoro group and a single hydroxy group. The AB monomers are reacted in the presence of a base in a dipolar solvent.

While not wishing to be bound by theory, the quinoline nucleus activates the fluoride leaving group towards nucleophilic substitution by providing favorable resonance forms for the intermediate Meisenheimer complex. The nitrogen atom of the quinoline nucleus can accept the negative charge of the incoming nucleophile. Positions on the quinoline nucleus which are most highly activated are the 2, 4, 5, and 7 positions. Resonance through phenylene groups is also possible and phenyl groups at the 2, 4, 5 and 7 positions of the quinoline nucleus, especially at the 2, and 4 positions of the quinoline nucleus, are activated at the 2 and 4 positions on the phenyl group.

There are two types of difluoro (type AA) monomers useful in accordance with the present invention, i.e., those which contain a single quinoline nucleus and those which contain two quinoline nuclei connected directly through a linking group. The general structure of the difluoro (AA) monomers useful in accordance with practice of the present invention which contain a single quinoline nucleus is given by the following structural formula:

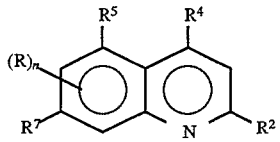

wherein $R^2$, $R^4$, $R^5$, and $R^7$ are selected from the group consisting of any groups which do not interfere with the polymerization reaction, including but not limited to alkyl, aryl, aryloxy, alkoxy, ketone, formyl (—COH), ester (—CO$_2$R' or OCOR'), amide (—NR'COR" or CONR'R"), heteroaryl, cyano, bridging groups (non-limiting examples of R bridging groups are —(CH$_2$)$_4$—, —(CH$_2$)$_3$—, and —CH=CH—CH=CH—), and F or ZF, wherein exactly two of $R^2$, $R^4$, $R^5$, $R^7$ are F or ZF, wherein Z is selected from the group nil, ortho-arylene, and para-arylene, and (R)$_n$ are any independently selected R groups, such as the $R^2$, $R^4$, $R^5$, $R^7$ groups listed above, which do not interfere with the polymerization reaction. The (R)$_n$ group(s) may be at any position on the quinoline nucleus not occupied by ZF or F. The R' and R" groups are alkyl or aryl.

Non-limiting examples of ortho-arylene are 1,2-phenylene, 1,2-naphthylenediyl, 2,3-naphthylenediyl, 1,2-(4-phenylphenylene), 1,2-(4-methoxyphenylene), and 1,2-(3-methylphenylene). Non-limiting examples of para-arylene are 1,4-phenylene, 1,4-naphthylenediyl, 1,4-(2-phenylphenylene), 1,4-(2-methoxyphenylene), and 1,4-(2,5-dimethylphenylene).

The general structure of the difluoro (AA) monomers useful in accordance with practice of the present invention which contain two quinoline nuclei is given by the following structural formula:

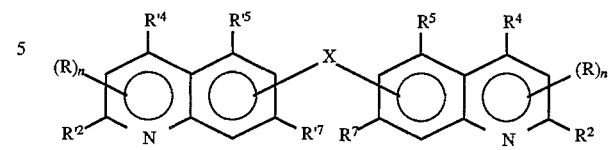

where $R^2$, $R^4$, $R'^2$, and $R'^4$ may be chosen independently from F and Z-F (where Z, as defined above is nil, ortho-arylene, and para-arylene); $R^5$, $R^7$, $R'^5$, and $R'^7$ may be F, and exactly one of $R^2$, $R^4$, $R^5$, and $R^7$ is F or Z-F and exactly one of $R'^2$, $R'^4$, $R'^5$, and $R'^7$ is F or Z-F, and the remaining positions on the quinoline nuclei are occupied by H or R, n is 0 to 5, (R)$_n$ are any independently selected R groups, where R is any group not interfering with the polymerization reaction including but not limited to alkyl, aryl, alkoxy, aryloxy, ketone, formyl (—COH), ester (—CO$_2$R' or OCOR'), amide (—NR'COR" or CONR'R"), heteroaryl, cyano and where two adjacent R groups may be bridging groups, non-limiting examples of R bridging groups are —(CH$_2$)$_4$—, —(CH$_2$)$_3$—, and —CH=CH—CH=CH—. The (R)$_n$ groups may be at any position of the quinoline nucleus, including either ring. The divalent linking group X links the two quinoline nuclei and may be attached at any position on either ring. The X groups can be any divalent group which does not interfere with the polymerization reaction (e.g. X should not contain strong nucleophiles like oxy anions, or good leaving groups like activated halides). The divalent linking group X may be chosen from:

nil,
—O—,
—S—,
—C(O)—,
—S(O)—,
—S(O$_2$)—,
—W—,
—(—O—W—)$_m$—O—, m=1–3, and
—Q—;

where W is a divalent group selected from the group consisting of:

—Ar'—(where Ar' means arylene),
—Het—(where Het means heteroarylene),
—Ar'—O—Ar'—,
—Ar'—C(O)—Ar'—,
—Ar'—S—Ar'—,
—Ar'—S(O)—Ar'—,
—Ar'—S(O)$_2$—Ar'—, and
—Ar'—Q—Ar'—,;

and where Q is a divalent group containing a quaternary carbon as shown below:

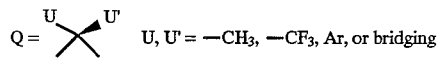

where if U and U' are bridging they may be alkylene, aryline, alkarylene, ether, ester, amide, alkylene ketone, arylene ketone, and may be partially or fully substituted with fluorine. Non-limiting examples of bridging U,U' groups are:

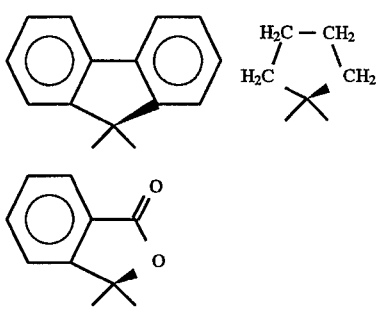

Non-limiting examples of arylene include 1,2-phenylene, 1,3-phenylene, 1,4-phenylene, 1,4-naphthylenediyl, 1,4-(2-phenylphenylene), 1,4-(2-methoxyphenylene), and 1,4-(2,5-dimethylphenylene). Non-limiting examples of heteroarylene include 2,4-pyridinediyl, 2,6-pyridinediyl, and 2,6-quinolinediyl.

Non-limiting examples of R groups described above are as follows:

alkyl groups are methyl, ethyl, propyl, isopropyl, tert-butyl, cyclohexyl, stearyl, and docosyl (—CH$_2$(CH$_2$)$_{20}$CH$_3$);

aryl groups are phenyl, biphenyl, naphthyl, anthracenyl, and diphenylphenyl;

C bound amides are N,N-dimethylaminocarbonyl (—CON(CH$_3$)$_2$), N,N-diphenylaminocarbonyl, piperidinecarbonyl (—CONCH$_2$CH$_2$CH$_2$CH$_2$CH$_2$), morpholinecarbonyl (—CONCH$_2$CH$_2$OCH$_2$CH$_2$), and N-methyl-N-phenylaminocarbonyl;

heteroaryl groups are pyridyl, quinolinedyl and pyrazyl;

N bound amides are benzoylamino, N-methylacetylamino;

O bound esters are acetyloxy (—OCOCH$_3$) and benzoyloxy (—OCOC$_6$H$_5$);

C bound esters are methoxycarbonyl (—CO$_2$CH$_3$) and phenoxycarbonyl (—CO$_2$C$_6$H$_5$);

aryloxy groups are phenoxy, naphthoxy, and biphenyloxy;

alkoxy groups are ethoxy and butoxy; and ketones are phenylketone (also called benzoyl), naphthylketone (naphthoyl), methylketone (acetyl), ethylketone (propionyl), tert-butylketone (pivaloyl), isobutylketone, trifluoromethylketone (trifluoroacetyl), methoxyethylketone, benzylketone, phenethylketone, 2,4,6-trimethylphenylketone, pyridinylketone (nicotinoyl), 2-quinolinoketone, and 2-thiopheneylketone.

Non-limiting Examples of difluoro (AA) quinoline monomers useful in accordance with practice of the present invention include 2-(2-fluorophenyl)-5-fluoro-4-phenylquinoline, 2-(4-fluorophenyl)-5-fluoro-4-phenylquinoline, 4-(2-fluorophenyl)-5-fluoro-2-phenylquinoline, 2-(4-fluorophenyl)-7-fluoro-4-phenylquinoline, 2,4-difluoroquinoline, 2,7-difluoroquinoline, 2,5-difluoroquinoline, 2,7-difluoro-6-phenylquinoline, and 4-(4-fluorophenyl)-7-fluoroquinoline.

Non-limiting examples of difluoro (AA) bis-quinoline monomers useful in accordance with practice of the present invention include 6,6'-bis[2-(4-fluorophenyl)-4-phenylquinoline, 6,6'-bis[2-(2-fluorophenyl)-4-phenylquinoline, 6,6'-bis[2-(4-fluorophenyl)-4-tert-butylquinoline, 6,6'-bis-[4-(4-fluorophenyl) -2-phenylquinoline, 6,6'-bis-4-fluoroquinoline, 6,6'-bis[4-(4-fluorophenyl)-2-(2-pyridyl)quinoline, 6,6'-bis-2-fluoroquinoline, 6,6'-bis[4-(4-fluorophenyl) -2-(methyl) quinoline, 6,6'-bis-[2-fluoro-4-phenylquinoline], oxy-bis-6,6'-[2-(4-fluorophenyl) -4-phenylquinoline], 1,4-benzene-bis-2,2'-[4-(4-fluorophenyl)quinoline], 1,4-benzene-bis-2,2'-[4-fluoroquinoline], 1,4-benzene-bis-4,4'-[2-(4-fluorophenyl)quinoline], and 1,1,1,3,3,3-hexafluoroisopropylidene-bis-(4-phenoxy-4-phenyl-2-(4-fluoroquinoline).

The (AA) monomers of the present invention may be prepared by coupling pre-formed chlorofluoroquinolines as shown, for example, in Examples 5 and 9 below. Alternatively, bis-aminobenzene derivatives may be condensed into bis-quinolines using the Friedlander or other quinoline-forming condensations known in the art. For example, in Example 1 below, 4,4'-diamino-3,3'-dibenzoylbiphenyl is condensed with 4-fluoroacetophenone to form an (AA) monomer. Use of 2-fluoroacetophenone would provide the corresponding 6,6'-bis-[2-(2-fluorophenyl)-4-phenylquinoline]. Similarly, condensation of 2-amino-4'-fluorobenzophenone with bis-ketomethylenes such as 4,4'-diacetylbiphenyl, 1,4-diacetylbenzene, and 4,4'-diacetylphenylether will give the corresponding (AA) monomers. Other bis-[ortho-aminobenzoylbenzene]s suitable for condensation to form (AA) monomers of the present invention are disclosed in U.S. Pat. No. 4,000,187. Other methods for synthesis of (AA)-type monomers will be readily apparent to those skilled in the art.

Non-limiting examples of fluorohydroxy (AB) monomers useful in accordance with practice of the present invention include: 2-(4-fluorophenyl)-6-hydroxy-4-phenylquinoline, 2-(2-fluorophenyl)-6-hydroxy-4-phenylquinoline, 4-(2-fluorophenyl)-6-hydroxy-2-phenylquinoline, 2,3-diphenyl-4-(2-fluorophenyl)-6-hydroxyquinoline, 2,3-diphenyl-4-(4-fluorophenyl)-6-hydroxyquinoline, 2,3-diphenyl-6-(2-fluorophenyl)-4-hydroxyquinoline, 2,3-diphenyl-6-(4-fluorophenyl)-4-hydroxyquinoline, 7-fluoro-2-hydroxyquinoline, 7-fluoro-2-hydroxy-4-phenylquinoline, 7-(4-fluorophenyl)-2-hydroxy-4-phenylquinoline, 7-fluoro-4-hydroxy-2-phenylquinoline, 7-(4-fluorophenyl)-4-hydroxy-2-phenylquinoline, 2-(4-fluorophenyl)-3-hydroxyquinoline, 2,-(4-fluorophenyl)-4-hydroxy-3-phenylquinoline, 2-(4-fluorophenyl)-6-hydroxy-3-phenylquinoline, 2-(4-fluorophenyl)-8-hydroxy-3-phenylquinoline, 2-(4-fluorphenyl)-8-hydroxyquinoline, and 2-(2-fluorophenyl)-4-(4-hydroxyphenyl)quinoline.

The (AB)-type monomers of the present invention may be prepared using any of the various methods for quinoline synthesis known in the art, including Friedlander synthesis, Skruap synthesis, Doebner synthesis, Niementowski synthesis, and the like. These quinoline-forming reactions are listed, for example, in The Merck Index, Tenth Edition, M. Windholz, Ed., Merck & Co., Rahway, N.J. 1983. The Merck Index, Tenth Edition, is incorporated herein by this reference. For example, the commercially available 2-amino-4-fluorobenzoic acid can be converted into 7-fluoro-4-hydroxyquinolines substituted at the 2 position with various groups derived from co-reactant α-methylene ketone derivatives by using the Niementowski synthesis. Various α-methylene ketone derivatives are described in U.S. Pat. No. 4,000,187. 3-aminophenol may be converted into hydroxyquinolines substituted at the 2 and/or 4 positions by condensations with acrolein derivatives (e.g., 4-fluorocinnamaldehyde) via the Doebner-Miller synthesis. Similarly, 2-aminophenol and 4-aminophenol may be condensed to give fluorohydroxyquinolines.

Diol (BB) monomers useful in accordance with practice of the present invention are of the structure H—Y—H, where Y is selected from —O— and —O—W—O— and W is as defined above.

Non-limiting examples of diol monomers useful as monomers of the present invention are hisphenol AF

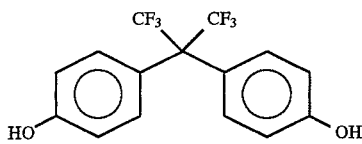

and 9,9-bis(4-hydroxyphenyl)fluorene.

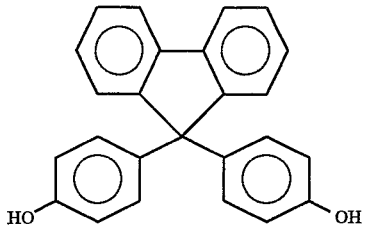

The diol monomers are present as a bis-oxide salt (e.g. dipotassium isopropylidene-bis-phenolate, and the like) or the reaction for preparing the polyquinolines of the invention is carried out in the presence of a base capable of deprotonating the diol. Such bases include alkali and alkali earth metal carbonates and hydroxides, such as potassium carbonate, potassium hydroxide, sodium carbonate, sodium hydroxide, and the like. Stronger bases such as sodium hydride or other metal hydrides, butyl lithium, sodamide or other metal amides, and the like may be used if the diol is not acidic enough to be sufficiently deprotonated by sodium hydroxide.

The diol (BB) monomers may be any diol which can be deprotonated under the polymerization conditions to give a nucleophilic oxy anion. Phenolic type diols, for example, may be deprotonated with bases such as potassium carbonate, sodium carbonate, sodium hydroxide, and the like, to give phenolate salts. The oxy anion may be formed separately and isolated, or preferably formed in situ. Water is typically produced when the base and diol react. This water may be removed, as described below, by azeotropic distillation. Use of diol monomers for other types of nucleophilic polymerizations is known in the art, for example, the polymerization of hydroquinone with 4,4'-difluorobenzophenone to form a polyetheretherketone (PEEK).

Other non-limiting examples of diol monomers useful in accordance with the present invention are resorcinol, hydroquinone, 4,4'-dihydroxybiphenyl, 1,3-dihydroxynaphthylene, 2,6-dihydroxynaphthlene, 2,7-dihydroxynaphthlene, 3,4'-dihydroxybiphenyl, 3,3'-dihydroxybiphenyl, methyl-2,4-dihydroxybenzoate, isopropylidenediphenol (bis phenol A), phenolphthalein, phenol red, 1,2-di(4-hyroxyphenyl)ethane, di(4-hydroxyphenyl)methane, and 4,4'-dihydroxybenzophenone. These and many other useful diol monomers are commercially available.

In one embodiment of the present invention the general structures of AB type monomers is given by:

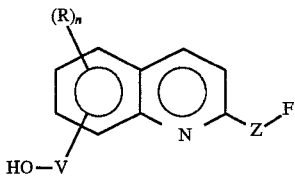

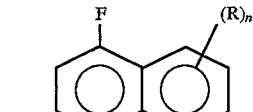

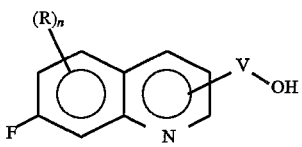

where Z is chosen from nil, ortho-arylene, and paraarylene, the V—OH group may be at any position of the quinoline nucleus including either ring, the group V may be chosen as any divalent group that does not interfere with the polymerization reaction, including but not limited to nil, alkylene, arylene, mixed alkylene/arylene, alkyleneoxy, arylenoxy, alkylene ketones, arylene ketones, arylene sulfone, alkylene sulfone, alkylene thioether, arylene thioether, and heteroarylene, and n is 0 to 5 and (R)$_n$ are any groups not interfering with the polymerization reaction including but not limited to alkyl, aryl, aryloxy, ketone, formyl, ester, amide, heteroaryl, cyano and bridging groups.

Non-limiting examples of V groups are as follows:
alkylene groups are methylene, ethylene and stearylene;
   arylene groups are phenylene and naphthylenediyl;
mixed alkyl/arylene groups are dimethylphenylene and ethylenephenylene (—CH$_2$CH$_2$—CH$_6$H$_4$—);
alkyleneoxy groups are methylenexoy and propyleneoxy;
aryleneoxy groups are naphthaleneoxy and phenyleneoxy;
alkylene ketone groups are methylene carbonyl and cyclohexylene carbonyl;
arylene ketone groups are methylphenylenecarbonyl and phenylenecarbonyl;
alkylene sulfone groups are methylene sulfone and ethanesulfone:
arylene sulfone groups are naphthalene sulfone and phenylene sulfone;
alkylene thioether groups are ethylenethio (—CH$_2$CH$_2$—S—) and propylenethio;
arylene thioether groups are biphenylenethio and phenylenethio (—C$_6$H$_4$—S—); and
heteroarylene groups are pyridinediyl and quinolinediyl.

The (R)$_n$ may be at any position of the quinoline nucleus not occupied by Z or V—OH, including either ring.

The polymers of the present invention result from nucleophilic displacement by an oxy anion of fluoride activated by a quinoline nucleus. These types of displacement reactions are best performed in an anhydrous dipolar solvent, non-limiting examples of which include N,N-dimethylformamide (DMF), N,N-dimethylacetamide (DMAC), N-methylpyrrolidinone (NMP), tetramethylurea, dimethylsulfoxide, sulfolane, and diphenylsulfone, or mixtures of these solvents with other anhydrous solvents. The addition of toluene, dichlorobenzene, or other solvent which forms an azeotrope with water may be desirable in order to azeotropically distill off water. In one embodiment, the diol monomer is allowed to react with potassium carbonate or other base to form the potassium salt, and byproduct water. This water is easily removed by azeotropic distillation (see examples). Isolation of the salt form of the diol monomer is not necessary, it may be formed and used in situ.

The general procedure for preparing polyquinoline polymers of the present invention comprises heating the monomer(s) and a base in an anhydrous solvent and azeotropically removing water (formed by the reaction of the base with the hydroxy groups on the BB or AB monomer). Alternatively, the BB or AB monomer(s) may be treated with base in a separate step and the corresponding oxide salt (bis-oxide salt for a BB monomer and oxide salt for AB monomer) isolated and purified as necessary. The order of addition of the reactants is not important. The amounts of the monomers used to from the polymers of the present invention may be determined by standard formulae known in the art, such as Carother's equation.

In general, (for AA+BB polymerization) while equal molar amounts of AA and BB monomers are normally used, molar ratios other than 1:1 may be used, if desired, to control the MW or end groups. Base is generally added in slight molar excess. For the solvent system NMP/toluene the reflux temperature is about 135° C., and water is collected over a six to eighteen hour period. The toluene or other co-solvent is then removed by distillation and the mixture brought to reflux (about 202° C. for NMP) and held for 12 to 24 hours, or until the desired polymer MW is achieved. Pressure is not critical; atmospheric pressure is preferred.

Endcappers, if desired, may be added at the beginning of the reaction, during the reaction, or near the end of the reaction. The polymer MW may be determined as is known in the art by measurement of viscosity or by gel permeation chromatography (size exclusion chromatography). The reaction is then cooled. The polymer may be recovered from the dope by any technique known in the art, including by precipitation with a non-solvent such as alcohol or water. The non-solvent is preferably chosen to be polar in order to remove fluoride salts which are the by-product of the reaction. It is also preferable to filter the polymer dope before precipitation. In some cases it may be desirable to dilute the dope before filtration or precipitation.

The AB monomers of the above described general structures may be polymerized to give polymers of the corresponding structures shown below:

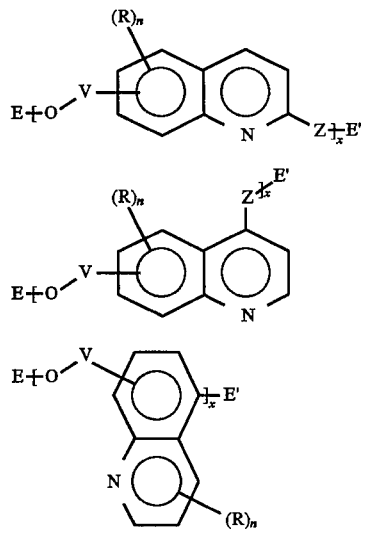

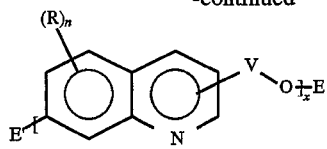

where E and E' are end groups and x is the number of repeat units. The number of repeat units x is preferably 2 to 1,000,000, more preferably 10 to 10,000, and most preferably 50 to 1000. If no endcappers are added, E is H and E' is F, except that adventitious endcappers derived from impurities and side reactions may also be present. Where E is H the chemical functional group at the polymer end is hydroxy. The reactivity of this end group is that of a hydroxy group. When speaking of the chemical nature of the end group it may be more appropriate to refer to E as hydroxy or OH, even though E is shown H. In the cases of the present invention, the most likely adventitious E' is —OH derived from water. Endcappers may be added intentionally; for example, phenol will yield a phenoxy endcap (E'=OPh), and 2-fluoroquinoline will yield a quinoline endcap (E=2-quinolyl).

The end groups can significantly alter the chemistry and reactivity of the product polymer. For example, fluoride end groups will be subject to nucleophilic attack, and can be further substituted by other nucleophiles. For example, the fluoride end group could be displaced by dyes or other labeled groups. A polymer having fluoride end groups could be reacted with a diol (possibly different than the original BB monomer diol) to form a new polymer of higher MW and possibly of a more complex structure. A polymer having fluoride end groups could be reacted with a trifunctional nucleophile, such as a triol, or a triamine, to form a branched or crosslinked polymer.

As in the case with fluoride end groups, hydroxy end groups are also reactive. Hydroxy end groups are acidic and when deprotonated by base are nucleophilic. These characteristics may be used in further reactions on the polymer, for example, to form esters or ethers. A hydroxy terminated polymer will react, for example, with a diacid chloride to form a polyester. Non-limiting diacid chlorides are adipoyl chloride, terephthaloyl chloride, succinoyl chloride, and the like. Hydroxy end groups may also be used to crosslink or form branched structures.

The nature of the end groups may also affect the thermal behavior of the polymers. The solubility of the polymers of the instant invention is changed on heating to high temperatures. For example, heating to 350° C. for two hours will cause the polymer of Example 2 below to become much less soluble in NMP. This is thought to be a result of further reaction of the end groups.

Exemplary polymers derived from the polymerization of AB monomers are shown below:

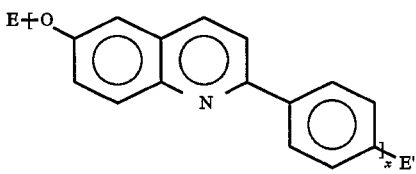

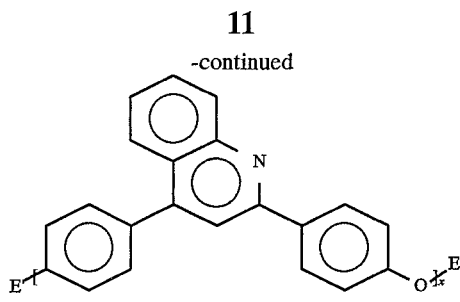

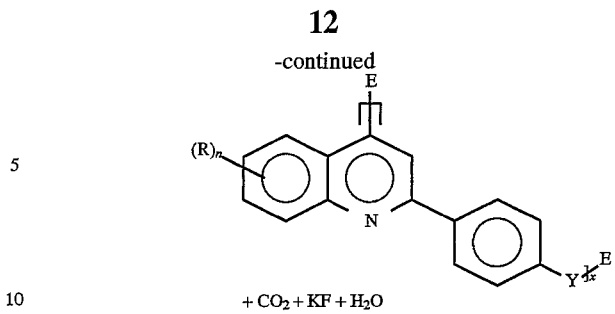

+ CO₂ + KF + H₂O

The single quinoline nucleus difluoro (AA) monomers may be allowed to react with diol (BB) monomers as is described below to form polymers having the general structure:

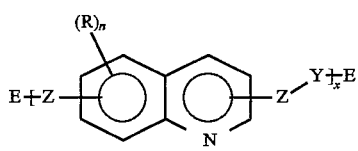 (1)

where $(R)_n$ and Z are as described above, and x is the number of repeat units, and the Z groups are attached to the quinoline nucleus at positions chosen from 2,4,5 and 7, and if a —Z—Y— group is attached to positions 5 or 7, then Z=nil, i.e., only Y is present, Y is a divalent moiety chosen from —O— and
—O—W—O—, where W is defined above, and E are end groups which depend on the relative amounts of AA and BB monomers present and on added endcappers.

In accordance with one embodiment of the present invention, the reaction of a difluoro (AA) single quinoline monomer with a diol monomer to produce a polyquinoline polymer under the general reaction conditions outlined above is exemplified by:

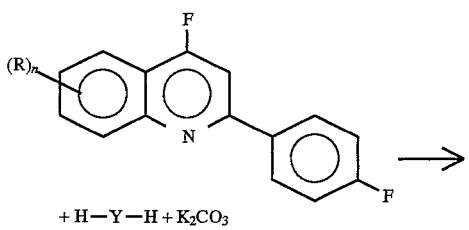

+ H—Y—H + K₂CO₃ →

The double quinoline nuclei difluoro (AA) monomers of the present invention may be used as described below to form polymers having ten general structures, the first three of which are shown below as structures (2), (3), and (4):

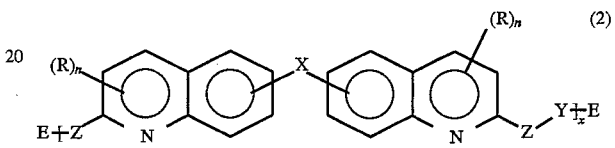 (2)

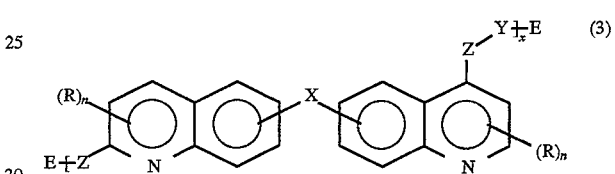 (3)

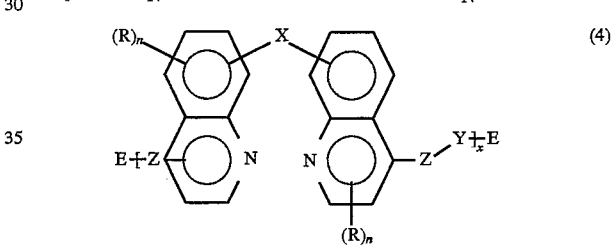 (4)

The seven additional general structures have the quinoline nuclei attached to the polymer chain through positions 2 and 5', 2 and 7', 4 and 5', 4 and 7', 5 and 5', 5 and 7', and 7 and 7'.

An exemplary embodiment of a more particular General Structure (2)-type Polyquinoline is given by the following structure:

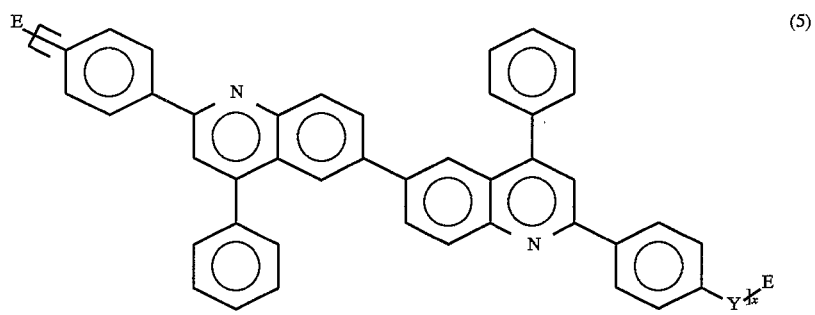 (5)

In the polymer of the structure 5, both Z's have been chosen as para-phenylene, $R^4$ and $R'^4$ have been chosen as R groups equal to phenyl, and all other R's are H.

A specific example of Structure 5 would be:

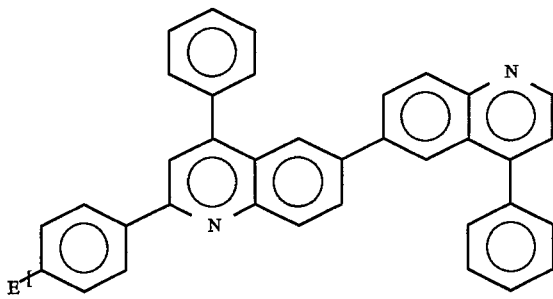
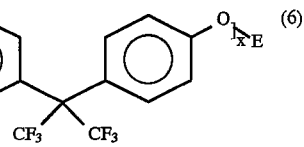

where the structure 6 polymer is formed by reacting the appropriate difluoro AA monomer with as bis-phenol AF, so that Y is bis-phenoxyhexa-fluoroisopropylidene, and X is nil. In structure 6, the end groups E are F and OH, as would occur if the two monomers were used in equal amounts; n is the number of repeat units.

Other specific structures falling under the General Structures will be apparent to those skilled in the art.

The following examples are illustrative of the present invention but are not considered limiting thereof in any way.

EXAMPLE 1

Preparation of a difluoroquinoline monomer of the structure:

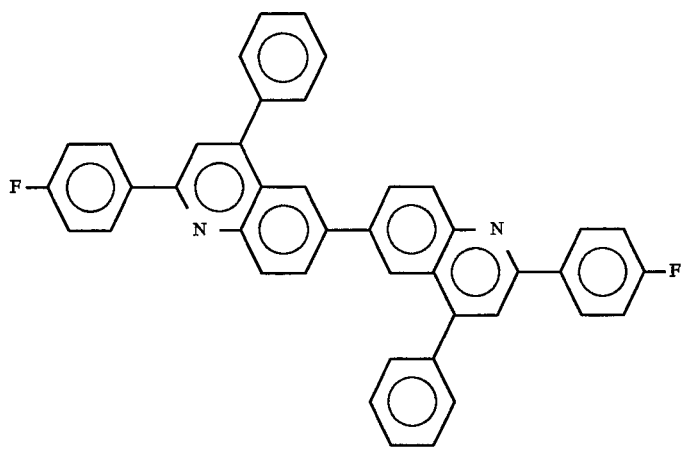

A 10 ml round-bottom flask was loaded with 1 g (2.56 mmol) 4,4'-diamino-3,3'-benzoylbiphenyl 0.4 g (2.89 mmol) 4-fluoroacetophenone and 0.1 g (0.52 mmol) toluene-sulfonic acid monohydrate. The open flask was heated to about 200° C. A color change from bright yellow to orange was apparent during the reaction, and water evaporated.

Continuous heating at 200° C. caused the product to crystallize. The flask was cooled and the crude solid was crushed and washed with hot ethanol. Further recrystallization gave monomer (7) with an 84% yield.

EXAMPLE 2

Preparation of a polyquinoline of the structure:

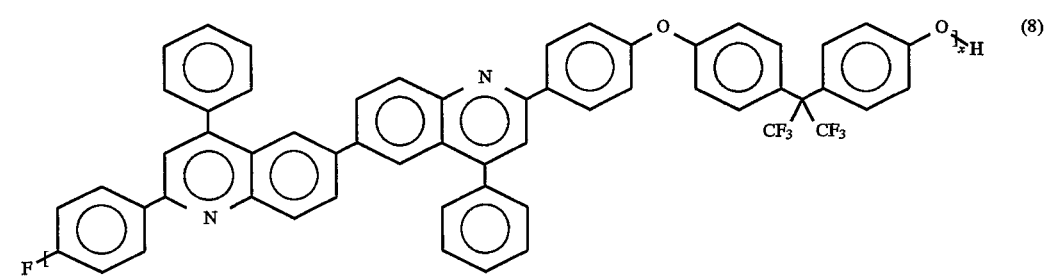

An oven-dried, three-necked, 100 mL round-bottomed flask equipped with a mechanical stirrer, a Dean-Stark trap, and a nitrogen inlet was charged with the difluoro quinoline monomer (7) (2.98 g, 5.0 mmol), bis-phenol AF (1.68 g, 5.0 mmol), potassium carbonate (1.04 g, 7.5 mmol), anhydrous NMP (20 mL), and toluene (20 mL). The mixture was heated to reflux (ca. 135° C.) under nitrogen (16 h). The toluene was removed, the Dean-Stark trap was replaced by a condenser, and the mixture was again heated at reflux (24 h). The reaction mixture was diluted with NMP (30 mL) and allowed to cool to room temperature. The polymer was precipitated by slowly pouring the solution into distilled water (250 mL). The solid was collected by filtration and dried under vacuum at 130° C. (yield>95%). $M_n$ =70,000 by GPC relative to polystyrene standards.

The polyquinoline polymer (8) has a $T_g$ of about 265° C. and is soluble in amide solvents, such as NMP, DMAC, and the like, and in some ether and ester solvents, including cyclopentanone and tetrahydrofuran. Polyquinoline (8) is insoluble in toluene, hexane, diethylether, water, acetone, and alcohols. Heating polyquinoline (8) to elevated temperatures of about 300° C. for about 1 to 10 hours increases the $T_g$ to about 280° C. and decreases the solubility.

EXAMPLE 3

Preparation of a controlled molecular weight polyquinoline of the structure:

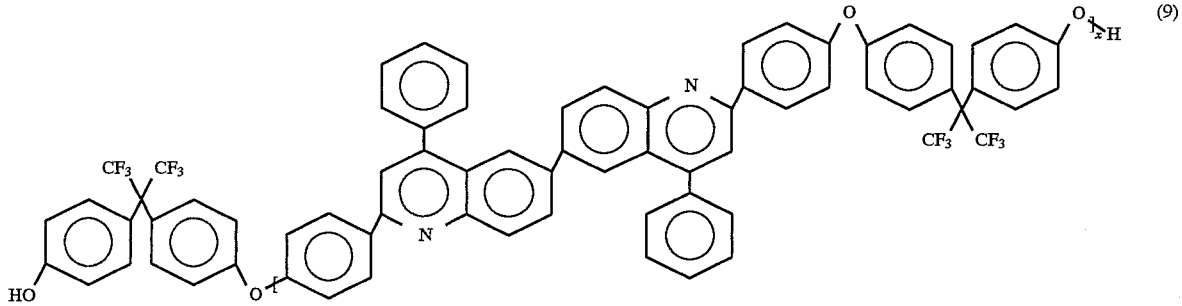

by monomer offset methods

An oven-dried, three-necked, 100 mL round-bottomed flask equipped with a mechanical stirrer, a Dean-Stark trap, and a nitrogen inlet was charged with the difluoroquinoline (7) (2.98 g, 5.0 mmol), bis-phenol AF (1.72 g, 5.1 mmol), potassium carbonate (1.04 g, 7.5 mmol), anhydrous NMP (20 mL), and toluene (20 mL). The mixture was heated to reflux (ca. 135° C.) under nitrogen (16 h). The toluene was removed, the Dean-Stark trap was replaced by a condenser, and the mixture was again heated at reflux (4 h). The reaction mixture was diluted with NMP (30 mL) and allowed to cool to room temperature. The polymer was precipitated by slowly pouring the solution into distilled water (25 mL). The solid was collected by filtration and dried under vacuum at 130° C. (yield>95%). $M_n$=36,000 by GPC relative to polystyrene standards.

EXAMPLE 4

Preparation of 6-chloro-2-(4-fluorophenyl)-4-phenylquinoline of the structure:

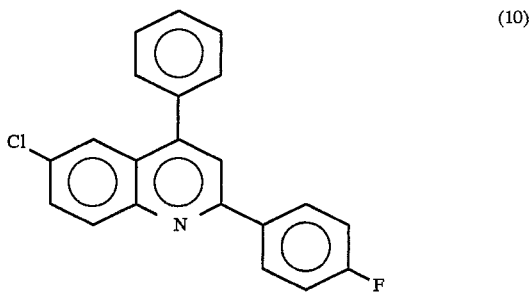

A three-necked, 2 L round-bottomed flask equipped with a thermometer, a mechanical stirrer, and a distillation unit fitted with a nitrogen inlet valve was charged with 2-amino-5-chlorobenzophenone (695.0 g, 3.00 mol), 4'-fluoroacetophenone (456.0 g, 3.30 mol), and p-tosic acid (47.62 g, 0.25 mol). The reaction mixture was heated under nitrogen at 165° C. (44 h). The yellow 4'-acetophenone that co-distilled with the water was separated and reintroduced to the reaction mixture through the heating period. The mixture was further heated to 190° C. (2 h). The mixture was cooled to 120° C. and poured into 95% ethanol (10 L) while vigorously stirring with a mechanical stirring rod setup. The mixture was filtered and the precipitate washed with ethanol (1 L). The solid was dried in a vacuum oven at 80° C. (16 h). Yield 969 g., 97%; mp 141.0°–142.1° C.

EXAMPLE 5

Preparation of 6,6'-bis[2-(4-fluorophenyl)-4-phenylquinoline]

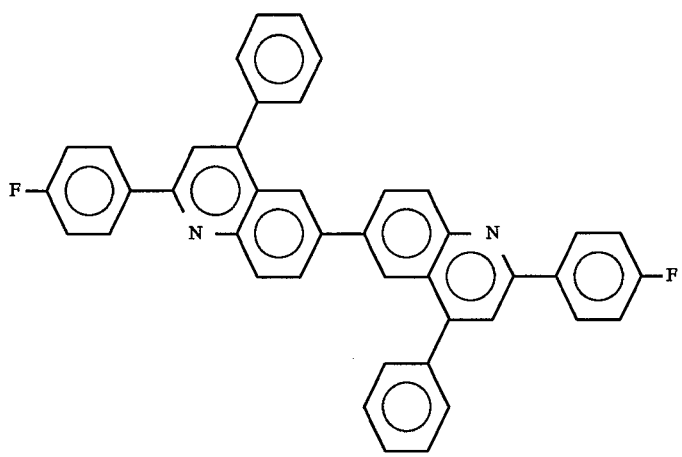
(7)

A 250 mL, three necked, round-bottomed flask fitted with a stirring rod set up and a nitrogen inlet was charged with Compound 10 (6-chloro-2-(4-fluorophenyl)-4-phenylquinoline) (25.0 g, 75 mmol), bis(triphenylphosphine)nickel dichloride (0.681 g, 1.04 mmol), sodium iodide (1.40 g, 9.37 mmol), triphenylphosphine (8.19 g, 33.3 mmol), and activated zinc dust (3.13 g, 47.9 mmol) and NMP (86 mL). The flask was heated under nitrogen to 70° C. (16 h). The mixture was diluted with NMP (10 mL), the temperature was raised to 170° C., and the mixture was filtered hot through Celite. The mother liquor was cooled to −20° C. and the product was collected by filtration. The yellow solid was washed with cold ethanol/methylene chloride (3/1) and was dried in a vacuum oven at 100° C. Yield 19.07 g, 85%, mp 280°–282° C. uncorrected.

EXAMPLE 6

Polymerizing the monomer of Example 5 (Compound (7)) with 9,9-bis(4-hydroxyphenyl) fluorene to provide a polyquinoline polymer of the following structure:

The solid was collected and dried under vacuum at 130° C. (12 h). Yield 170 g, 99%; $M_n$=46,900 by GPC relative to polystyrene standards. Polyquinoline 11 has a $T_g$ of about 306° C.

EXAMPLE 7

Polymerizing the monomer of Example 5 (Compound (7)) with 1,4-hydroquinone to provide a polyquinoline polymer of the following structure:

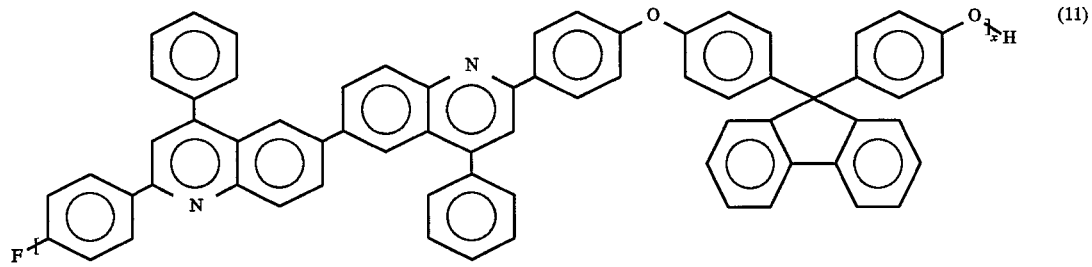
(11)

A three-necked, 2 L round-bottomed flask equipped with a mechanical stirrer, a Dean-Stark trap fitted with a condenser and a nitrogen inlet valve, and a thermometer was charged with Compound (7) provided in Example 5 (114.75 g, 0.19225 mol, 1.03 eq), 9,9-bis(4-hydroxyphenyl)fluorene (66.0472 g, 0.18848 mol, 1.00 eq), potassium carbonate (39.1 g, 0.28 mol, 1.5 eq), NMP (705 mL), and toluene (421 mL). The reaction mixture was heated to reflux under nitrogen (15 h). The toluene was removed through the Dean Stark trap, and the reaction was further heated at 200° C. (12 h). The reaction mixture was diluted with NMP and cooled to room temperature. The polymer was coagulated by slowly pouring the resulting polymer solution into acetone (ca. three volumes). The solid was collected by filtration, dissolved in NMP, and coagulated in water (ca. three volumes).

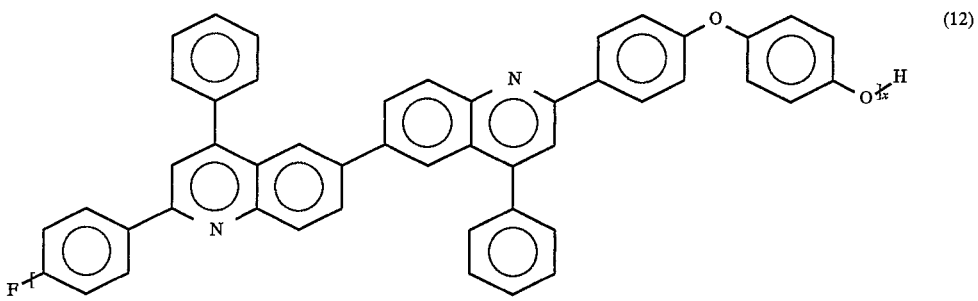

A three-necked, 100 mL, round-bottomed flask equipped with a mechanical stirrer, a Dean-Stark trap fitted a condenser and a nitrogen inlet valve, and a thermometer was charged with Compound (7) provided in Example 5 (2.00 g, 3.35 mmol); 1,4-hydroquinone (0.369 g, 3.35 mmol); potassium carbonate (1.02 g, 7.38 mmol); anhydrous NMP (18 g); and toluene (15 g). The reaction mixture was heated to reflux (ca. 160° C.) under nitrogen (4 h). The toluene was removed through the Dean Stark trap, and the reaction was further heated at 202° C. (16 h). The reaction mixture was cooled to room temperature and diluted with NMP. The polymer was coagulated by slowly pouring the resulting polymer solution into ethanol. The solid was collected by filtration and was stirred in hot ethanol (2 h). The solid was again collected and dried in a vacuum oven at 150° C. (12 h). $M_n$=77,900 by GPC relative to polystyrene standards.

EXAMPLE 8

Polymerizing the monomer of Example 5 (Compound (7)) with bis-phenol A to provide a polyquinoline polymer of the following structure:

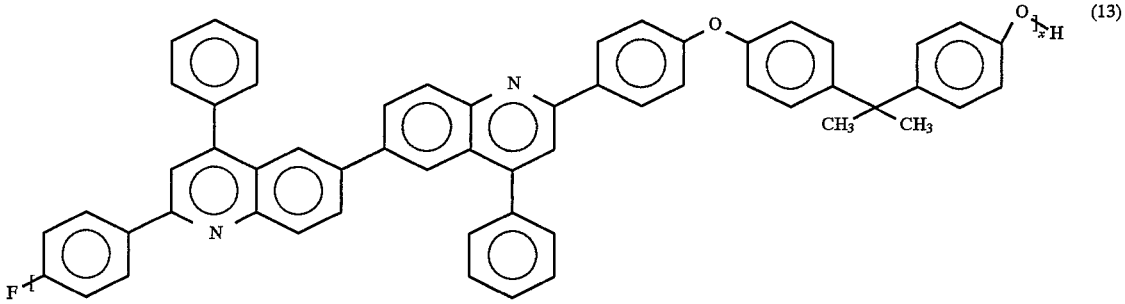

A three-necked, 500 mL, round-bottomed flask equipped with a mechanical stirrer, a Dean-Stark trap fitted a condenser and a nitrogen inlet valve, and a thermometer was charged with Compound (7) provided in Example 5 (17.9 g, 30.0 mmol), bis-phenol A (6.85 g, 30.0 mmol), potassium carbonate (6.22 g, 45.0 mmol), NMP (120 mL), and toluene (120 mL). The reaction mixture was heated to reflux under nitrogen (12 h). The toluene was removed through the Dean Stark trap, and the reaction was further heated at 202° C. (10 h). The reaction mixture was diluted with NMP (125 mL) and was cooled to room temperature. The polymer was coagulated by slowly pouring the resulting polymer solution into methanol (ca. 1 L). The solid was collected by filtration, dissolved in NMP (250 mL), and coagulated in water (ca. 1 L). The solid was again collected by filtration and was boiled in methanol (1 h). The polymer was collected and was dried in a vacuum at 100° C. (12 h). Yield 22 g, 93%; $M_n$=25,500 by GPC relative to polystyrene standards.

EXAMPLE 9

Preparation of 6,6'-bis[2-(4-fluorophenyl)-4-phenylquinoline](Compound 7) without isolation of compound (10)

A 250 mL, three-necked, round-bottomed flask fitted with a mechanical stirring set-up, a short path distillation apparatus, and a nitrogen inlet valve was charged with 2-amino-5-chlorobenzophenone (Compound 3) (17.4 g, 75.0 mmol), 4'-fluoroacetophenone (Compound 2) (10.0 mL, 824 mmol), and tosic acid (0.505 g, 2.7 mmol). The reaction was heated under nitrogen at 180° C. (20 h) to effect water removal. The temperature of the reaction was lowered to 160° C., and potassium carbonate (0.367 g, 2.7 mmol) was added. Toluene (100 mL) was then added to the reaction and distilled away. This toluene addition/distillation was repeated two times.

The temperature of the reaction was lowered to 80° C., and the distillation unit was removed. The flask was charged with nickel chloride (0.778 g, 6.00 mmol), sodium iodide (2.43 g, 16.2 mmol), tris(2-tolyl)phosphite (6.77 g, 19.2 mmol), and NMP (63 mL), and the resulting solution was stirred (18 h). The reaction temperature was then lowered to 60° C., and zinc powder (6.59 g, 101 mmol) was added. After the exotherm had subsided (10 min), the reaction was allowed to stir at 80° C. (16 h).

The temperature of the reaction was raised to 160° C. to dissolve the precipitate which had formed. The reaction mixture was filtered while hot through Celite and was allowed to cool to room temperature. The crude product was collected by filtration and was washed with ethanol. A second crop was collected from the mother liquor and was washed with ethanol. The yellow product was dried in a vacuum oven at 160° C. (18 h). 12.0 g from Crop 1 and 6.3 g from Crop 2 (Yield 73.1%).

EXAMPLE 10

Alternate preparation of 6,6'-bis[2-(4-fluorophenyl)-4-phenylquinoline](Compound 7) without isolation of compound (10)

A 250 mL, three-necked, round-bottomed flask fitted with a nitrogen inlet, a stirring rod set up, and a distillation unit was charged with 2-amino-5-chlorobenzophenone (17.38 g, 75.0 mmol), 4'fluoroacetophenone (10.0 mL, 82.0 mmol), and p-tosic acid (1.00 g, 5.3 mmol). The reaction was heated to 180° C. under nitrogen (16 h). The water that was produced was discarded and toluene (2×50 mL) was successively added to the reaction mixture and removed through the distillation set up.

The reaction was cooled to room temperature and a mixture containing bis(triphenylphosphine)nickel dichloride (0.681 g, 1.04 mmol), sodium iodide (1.40 g, 9.37 mmol), triphenylphosphine (8.19 g, 33.3 mmol), and zinc powder (3.13 g, 47.9 mmol) were added to the reaction flask along with NMP (86 mL). The flask was heated under nitrogen to 70° C. (16 h). The mixture was diluted with NMP (10 mL), the temperature was raised to 170° C., and the mixture was filtered through Celite. The mother liquor was cooled to −20° C. and the product was collected by filtration. The yellow solid was washed with cold ethanol/methylene chloride (3/1) and was dried in a vacuum oven at 100° C. Yield 18.03 g, 80.5%.

EXAMPLE 11

Preparation of Activated Zinc Dust

Activated zinc dust is obtained after 2 washings of commercially available 325 mesh zinc dust with 1M hydrogen chloride in diethyl ether (anhydrous) followed by 2 washings with diethyl ether (anhydrous) and drying in vacuo or under inert atmosphere for several hours at about 100°–200° C. If clumps form during drying the zinc dust is re-sieved to −150 mesh. This material should be used immediately or stored under an inert atmosphere away from oxygen and moisture.

The polymer compositions of the present invention are generally useful in the area of electronics and microelectronics applications because of their combination of low dielectric constant, low water uptake, high thermal stability and good solubility. The instant polymers are useful for dielectric layers in integrated circuits (IC's) such as planarizers, insulators, passivation layers, encapsulants, adhesives and the like. They are also useful in various wiring board applications, such as printed wiring boards, flexible wiring boards, tape automated bonding substrates, multi-chip modules, dielectrics, other high density interconnect devices, and the like. They may also be used in fabrication of electronic components such as capacitors, resistors, discrete semiconductor devices, inductors, or other devices requiring an insulating layer.

The polymers of the present invention are also useful in electrical applications such as wire coatings and insulation, insulating lacquers, for fabricating molded connectors, switches, enclosures, insulating strips, or the like. Other applications requiring low dielectric constant and good mechanical properties are coatings applications, especially where high thermal stability and transparency are desired, and insulating applications, including conformal coatings and protective layers, potting compounds, and the like. The polymers of the present invention are also useful as adhesives, for example as die attach adhesives, optionally with fillers, or laminate adhesives. The polymers of the present invention are also useful as matrix resins for composites.

The instant polymers may also be used as free standing films, as laminated films, fibers, and coatings.

The following examples of applications for the polymers of the present invention are intended to be illustrative and are in no way limiting.

Referring to FIG. 1, a semi-schematic cross-sectional side view of a multi-chip module 10, provided in accordance with practice of the present invention, is shown. Such multi-chip modules are wiring boards designed to hold several integrated circuit chips (IC's) (not shown) directly without the IC's first being packaged into individual chip carriers. The multi-chip module is typically (but not necessarily) fabricated using photolithographic techniques similar to those used in IC fabrication. The following procedure outlining multi-chip module fabrication is illustrative and many variations are known in the art and may be used with the present invention.

A substrate 12, typically a four- or six-inch silicon or alumina wafer having a plurality of conductors 13 on its surface, is spin-coated with a layer 14 of a polyquinoline polymer provided in accordance with the present invention. Solvent from the spin-coating process is removed in an oven, and the polyquinoline layer is cured by heating to a selected temperature for a selected period of time as described above to enhance the solvent resistance of the polyquinoline layer. Vias (not shown) are cut through the polymer by any of several techniques, for example, laser drilling or patterning and etching. A layer of metal 16, typically copper or aluminum, is deposited and patterned using techniques known in the art to form metal lines with a portion of the metal 16a extending through the via and contacting the conductors 13. A second layer of polyquinoline 18 provided in accordance with the present invention is spin-coated, dried and cured, completely covering the underlying metal. Vias are cut as above, and a second layer of metal is deposited and patterned. Additional layers of polymer 20 and metal 22 are added by repeating the above procedure. In some processes, it may be desirable to use adhesion promoters to enhance adhesion of the polymer to the silicon substrate or subsequent layers, or to plate the metal lines with chromium or gold before the application of the polymer.

The polymers of the present invention are also useful as dielectric materials in other passive or active discrete electronic components, such as capacitors, resistors, inductors, transformers, diodes, transistors and the like.

Figure 2:
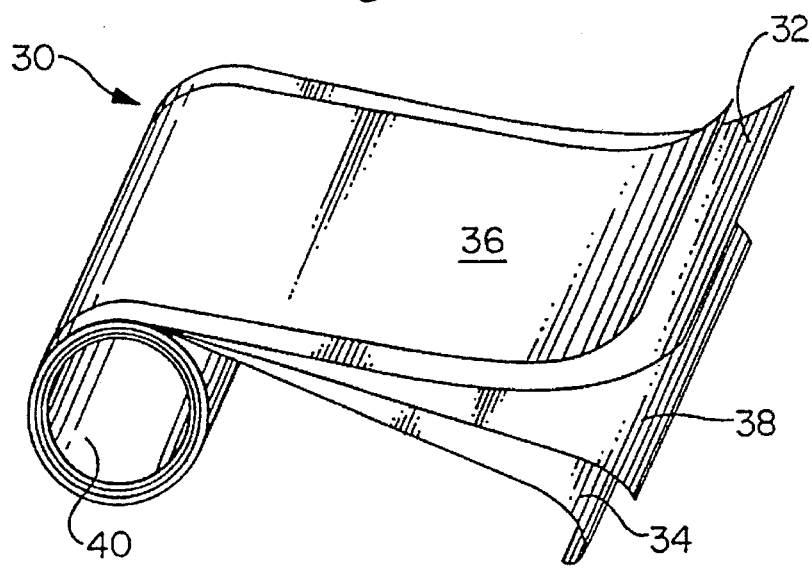
FIG. 2 is a semi-schematic exploded perspective view of a capacitor provided in accordance with the present invention.

Referring to FIG. 2, a semi-schematic exploded view of a capacitor 30 is shown. Dielectric films 32, and 34, comprising a polyquinoline polymer provided in accordance with practice of the present invention, insulate metal foils 36, and 38, which form the plates of the capacitor. The multi-layer structure is typically wound into a roll 40, and packaged after providing electrical connections (not shown).

The polymers of the present invention may also be used in coating applications such as liquid crystal displays, flat panel TV, light valves, solar windows, and the like. The instant polymers are also useful in optic and electro-optic applications such as optical wave guides, optical fibers, and non-linear optical devices. Electrical applications include wire coatings and wire wrap film, protective and anticorrosion coatings, as resin for connectors, housing, switches, plugs, sockets, or other molded electrical components.

The polymers of the present invention are also useful as interlayer dielectrics for integrated circuits. The low dielectric constant and high thermal stability are advantageous in interlayer dielectric applications. The interlayer dielectric separates the signal-carrying metal layers from each other and/or from the semi-conductor devices of the integrated circuit.

Figure 3:
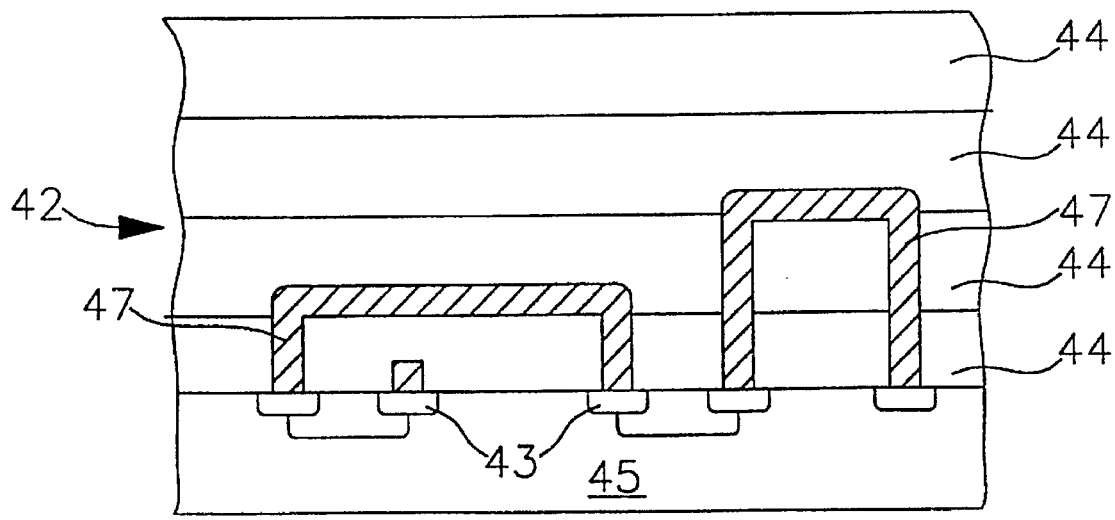
FIG. 3 is a semi-schematic cross-sectional side view of an integrated circuit provided in accordance with practice of the present invention.

Turning to FIG. 3, there is shown a schematic view of an integrated circuit 42, comprising a semi-conducting device 43, integrated into a silicon wafer 45, metal signal-carrying lines 47, and a polyquinoline polymer provided in accordance with practice of the present invention serving as insulating dielectric layers 44. The polyquinoline layers are fabricated using techniques commonly known in the art, including spin-coating followed by curing at elevated temperature.

The polyquinoline polymers of the present invention are also useful as coatings where high transmission to visible light is desired. Coatings for use in other harsh environments, such as industrial, petrochemical, chemical, are also applications of the instant polymers.

The polyquinoline polymers of the present invention may also be formed into fibers, by methods known in the art, such as wet spinning, dry spinning, and extrusion, and subject to further treatments such as hot or cold drawing.

Figure 4:
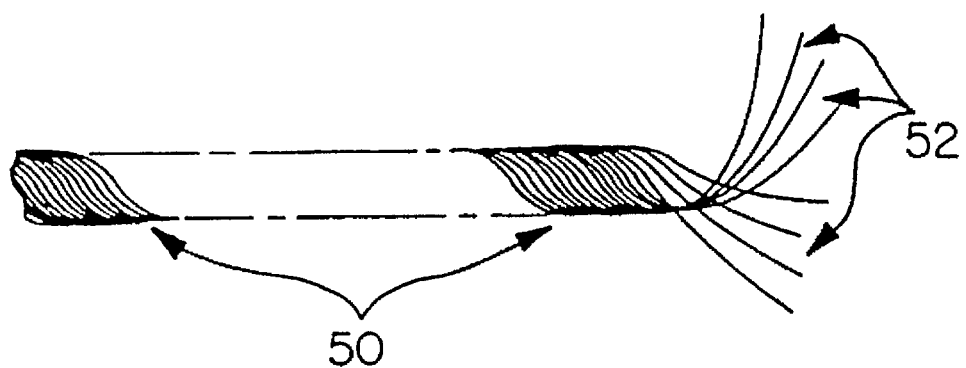
FIG. 4 is a semi-schematic perspective view of a multi-filament fiber provided in accordance with practice of the present invention.

Turning to FIG. 4, there is shown a semi-schematic view of a multi-filament fiber 50, comprising a plurality of mono-filaments 52 of a polyquinoline polymer, provided in accordance with the present invention.

High strength, thermally stable films, optionally uniaxially oriented, may be prepared from the polyquinoline polymers of the present invention.

Figure 5:
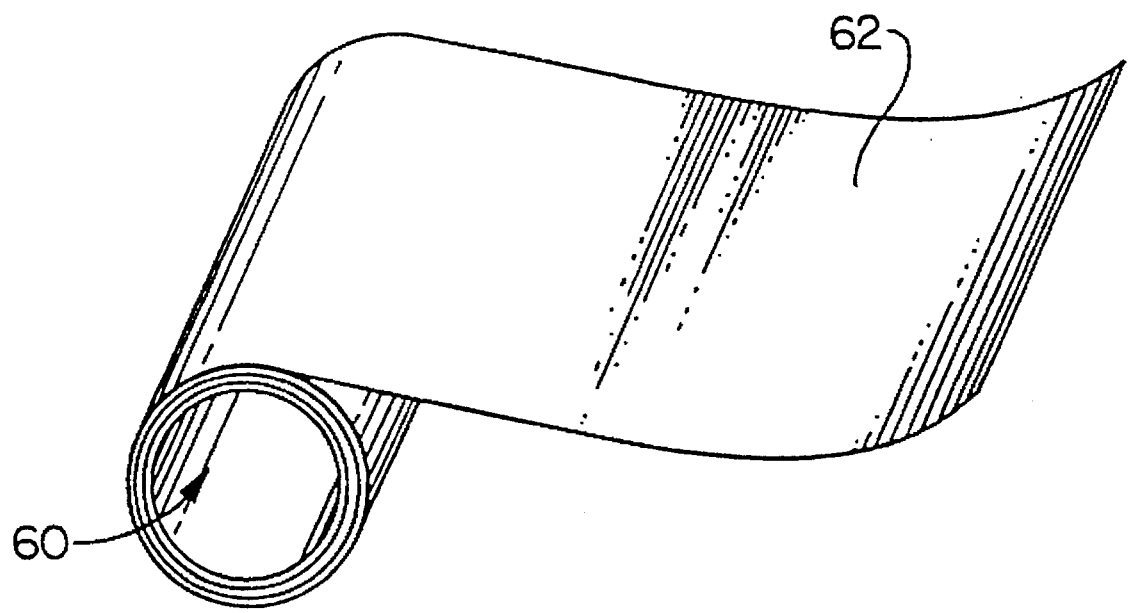
FIG. 5 is a semi-schematic perspective view of a roll of free-standing film provided in accordance with practice of the present invention.

Turning to FIG. 5, there is shown a roll 60 of free-standing film 62, formed from a polyquinoline polymer prepared in accordance with practice of the present invention.

The above-described fibers and films have various uses, including textiles, cord, rope, fibers for use in composites, barrier films, bagging material, electrical and thermal insulation, and release films.

The polymers of the present invention may also be used as matrix resins for composites applications.

The above description of preferred embodiments of polyquinoline polymers and the monomers useful for forming the polymers are for illustrative purposes. Because of variations which will be apparent to those skilled in the art, the present invention is not intended to be limited to the particular embodiments described above. The invention disclosed herein may suitably be practiced in the absence of any material or composition which is not specifically disclosed herein. The scope of the invention is defined in the following claims.

What is claimed is:

1. A method for preparing a polyquinoline polymer comprising the steps of:

a) providing a monomer comprising two fluoro groups, wherein each fluoro group is activated by a quinoline nucleus;

b) providing a diol monomer present as its bis-oxide salt or in the presence of a base deprotonating the diol; and c) reacting the monomer comprising two fluoro groups with the diol monomer in a dipolar solvent to thereby form the polyquinoline polymer.

2. The method according to claim 1, wherein the monomer comprising two fluoro groups has the following structure:

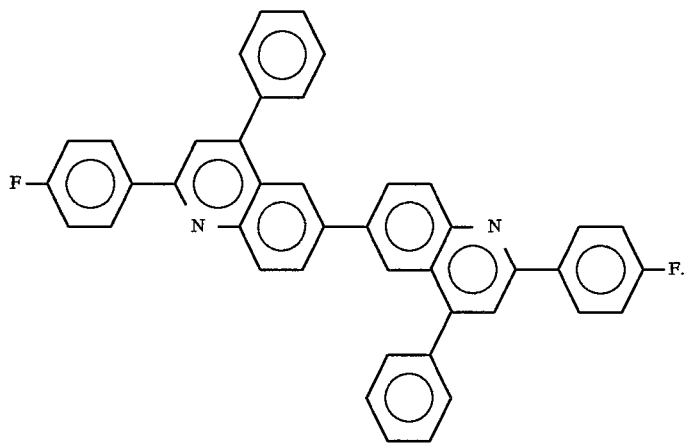

3. The method according to claim 1, wherein the diol monomer has the following structure:

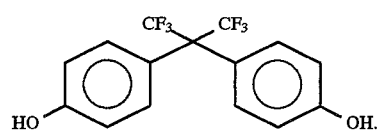

4. The method according to claim 1, wherein the monomer comprising two fluoro groups has the structure:

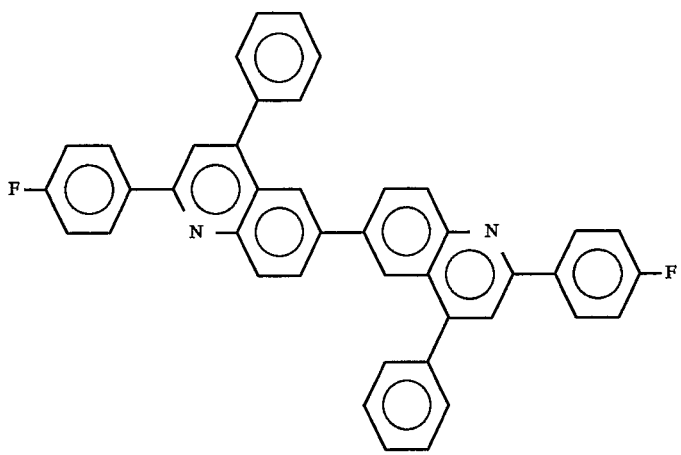

and the diol monomer has the structure:

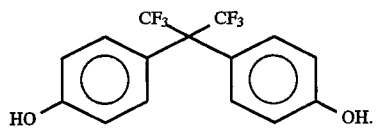

5. The method according to claim 1, wherein the monomer comprising two fluoro groups has the structure:

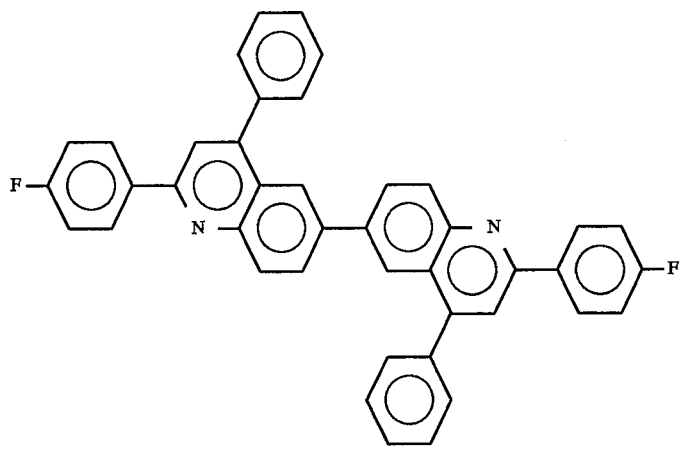

and the diol monomer has the structure:

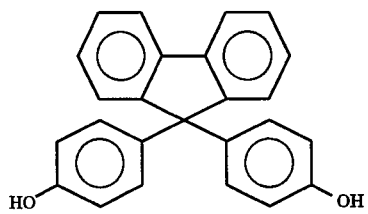

6. The method according to claim 1, wherein at least two different monomers comprising two fluoro groups are present, so that the polyquinoline polymer is a copolymer.

7. The method according to claim 6, wherein the diol monomer has the following structure:

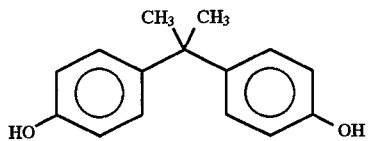

8. A method for preparing a polyquinoline polymer, the method comprising polymerizing a fluorohydroxy monomer comprising a quinoline nucleus containing one activated fluoro group and one hydroxy group in the presence of a base in a dipolar solvent to thereby form said polyquinoline polymer.

9. The method according to claim 8, wherein at least two different fluorohydroxy monomers are present and the polyquinoline polymer is a copolymer.

10. The method according to claim 8 additionally comprising providing at least one additional monomer comprising two fluoro groups activated by a quinoline nucleus, and polymerizing the additional monomer with the fluorohydroxy monomer to a produce a polyquinoline polymer that is a copolymer.

11. The method according to claim 8 additionally comprising providing at least one additional monomer, the additional monomer being a diol monomer, present as its bis-oxide salt or in the presence of a base deprotonating the diol, and polymerizing the additional monomer with the fluorohydroxy monomer to produce a the polyquinoline polymer that is a copolymer.

12. A method for preparing a polyquinoline polymer, the method comprising the steps of:

a) providing a monomer comprising a quinoline nucleus containing one activated fluoro group and one hydroxy group;

b) treating the monomer with a base to form the oxide salt; and c) reacting the oxide salt of said monomer in a dipolar solvent to thereby form the polyquinoline polymer.

13. A polymer comprising repeat units having at least one quinoline nucleus and at least one ether linkage and having as end groups either fluoro groups or hydroxy groups or a combination of fluoro and hydroxy groups.

14. The polymer of claim of claim 13, wherein the structure of each repeat unit is

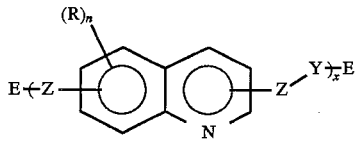

wherein (R) is any group which does not interfere with the polymerization reaction; n=0 to 5, Z is selected from the group consisting of nil, ortho-arylene containing 6 to 12 carbon atoms and para-arylene containing 6 to 12 carbon atoms; Y is selected from the group consisting of —O— and —O—W—O— wherein W is a divalent group containing 6 to 20 carbon atoms and is selected from the group consisting of alkylene, arylene, alkarylene, ether, ester, amide, alkylene ketone, arylene ketone and may be partially or fully substituted with fluorine; x is the number of repeat units; and E is an end group independently selected from the group consisting of fluoro and hydroxy groups.

15. The polymer of claim 13, wherein the structure of each repeat unit is

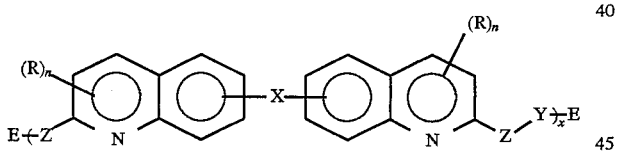

wherein (R) is any group which does not interfere with the polymerization reaction; n=0 to 5, Z is selected from the group consisting of nil, ortho-arylene containing 6 to 12 carbon atoms and para-arylene containing 6 to 12 carbon atoms; Y is selected from the group consisting of —O— and —O—W—O— wherein W is a divalent group containing 6 to 20 carbon atoms and is selected from the group consisting of:
—Ar'—,
—Het'—,
—Ar'—O—Ar'—,
—Ar'—C(O)—Ar'—,
—Ar'—S—Ar'—,
—Ar'—S(O)—Ar'—,
—Ar'—S(O)$_2$—Ar'—, and
—Ar'—Q—Ar'—;

wherein Ar' is an arylene group containing 6 to 12 carbon atoms, Het' is a heteroarylene containing 5 to 9 carbon atoms, and wherein Q is a divalent group containing a quaternary carbon as shown below:

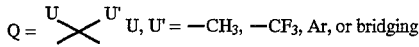

wherein if U and U' are bridging, U and U' have 1 to 6 carbon atoms, respectively, and are selected from the group consisting of alkylene, arylene, alkarylene, ether, ester, amide, alkylene ketone, arylene ketone, optionally, partially or fully substituted with fluorine; x is the number of repeat units; and E is an end group independently selected from the group consisting of fluoro, H, and hydroxy groups.

16. The polymer of claim 13, wherein the structure of each repeat unit is

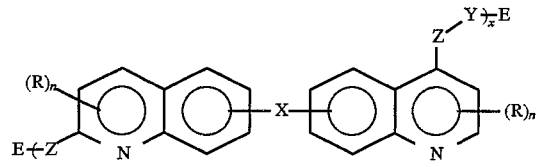

wherein (R) is any group which does not interfere with the polymerization reaction; n=0 to 5, Z is selected from the group consisting of nil, ortho-arylene containing 6 to 12 carbon atoms and para-arylene containing 6 to 12 carbon atoms; Y is selected from the group consisting of —O— and —O—W—O— wherein W is a divalent group containing 6 to 20 carbon atoms and is selected from the group consisting of:
—Ar'—,
—Het'—,
—Ar'—O—Ar'—,
—Ar'—C(O)—Ar'—,
—Ar'—S—Ar'—,
—Ar'—S(O)—Ar'—,
—Ar'—S(O)$_2$—Ar'—, and
—Ar'—Q—Ar'—;

wherein Ar' is an arylene group containing 6 to 12 carbon atoms, Het' is a heteroarylene containing 5 to 9 carbon atoms, and wherein Q is a divalent group containing a quaternary carbon as shown below:

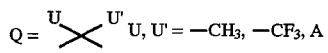

wherein if U and U' are bridging, U and U' have 1 to 6 carbon atoms, respectively, and are selected from the group consisting of alkylene, arylene, alkarylene, ether, ester, amide, alkylene ketone, arylene ketone, optionally, partially or fully substituted with fluorine; x is the number of repeat units; and E is an end group independently selected from the group consisting of fluoro, H, and hydroxy groups.

17. The polymer of claim 13, wherein the structure of each repeat unit is

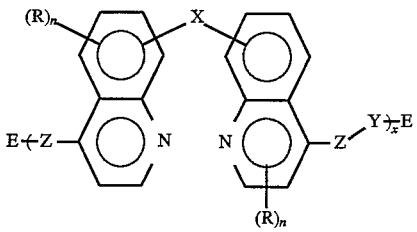

wherein (R) is any group which does not interfere with the polymerization reaction; n=0 to 5, Z is selected from the group consisting of nil, ortho-arylene containing 6 to 12 carbon atoms and para-arylene containing 6 to 12 carbon atoms; Y is selected from the group consisting of —O— and —O—W—O— wherein W is a divalent group containing 6 to 20 carbon atoms and is selected from the group consisting of:

—Ar'—,
—Het'—,
—Ar'—O—Ar'—,
—Ar'—C(O)—Ar'—,
—Ar'—S—Ar'—,
—Ar'—S(O)—Ar'—,
—Ar'—S(O)$_2$—Ar'—, and
—Ar'—Q—Ar'—;

wherein Ar' is an arylene group containing 6 to 12 carbon atoms, Het' is a heteroarylene containing 5 to 9 carbon atoms, and wherein Q is a divalent group containing a quaternary carbon as shown below:

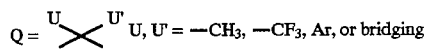

Q = U—C—U'   U, U' = —CH$_3$, —CF$_3$, Ar, or bridging wherein if U and U' are bridging, U and U' have 1 to 6 carbon atoms, respectively, and are selected from the group consisting of alkylene, arylene, alkarylene, ether, ester, amide, alkylene ketone, arylene ketone, optionally, partially or fully substituted with fluorine; x is the number of repeat units; and E is an end group independently selected from the group consisting of fluoro, H, and hydroxy groups.

18. The polymer of claim 13, wherein the structural formual of said polymer is:

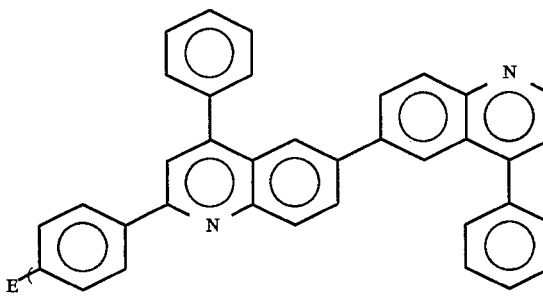

and where E is independently selected from the group consisting of fluoro and H.

19. The polymer of claim 13, wherein the structural formula of said polymer is:

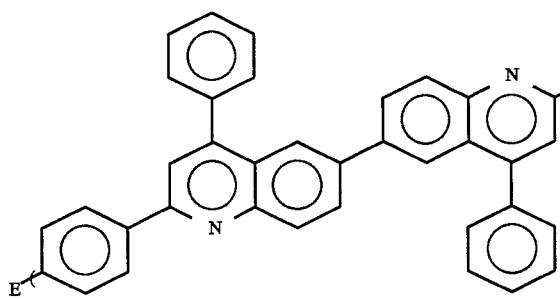

and where E is independently selected from the group consisting of fluoro and H.

20. The polymer of claim 13, wherein the structural unit of said polymer is selected from the group consisting of:

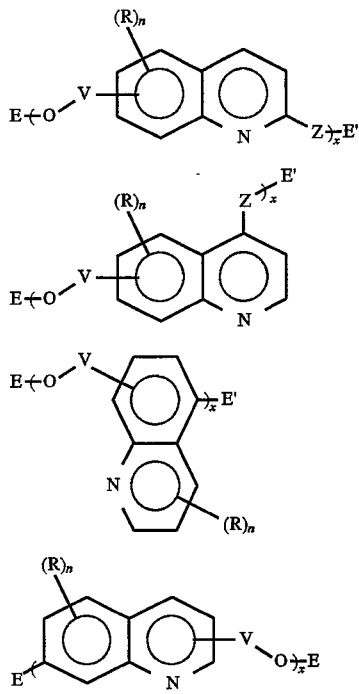

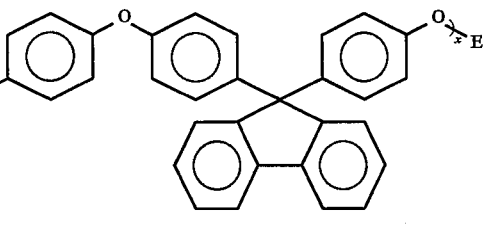

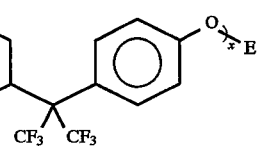

wherein E and E' are independently selected from the group consisting of fluoro, hydroxy and H, Z is selected from the group consisting of nil, ortho-arylene containing 6 to 12 carbon atoms, and para-arylene containing 6 to 12 carbon atoms, —V—O— linkage in the structural formula may be at any position of the quinoline nucleus including either ring, V being selected from the group consisting of nil, alkylene, arylene, mixed alkyl/ arylene, alkyl/arylene ethers, alkyl/arylene ketones, alkyl/arylene sulfones, alkyl/arylene thioethers, and heteroarylenes, the alkylene groups containing 1 to 18 carbon atoms, the arylene groups containing 6 to 12 carbon atoms, the heteroarylene groups being pyridinediyl and quinolinediyl, and n is 0 to 5, and $(R)_n$ represent groups selected from the group consisting of alkyl groups containing 1 to 22 carbon atoms, aryl groups containing 6 to 18 carbon atoms, aryloxy groups containing from 6 to 18 carbon atoms, ketone, formyl, ester, amide, heteroaryl groups selected from pyridyl quinolyl and pyrazyl, cyano and bridging groups.

* * * * *